(12) United States Patent
D'Angelico et al.

(10) Patent No.: US 9,423,287 B2
(45) Date of Patent: Aug. 23, 2016

(54) APPARATUS FOR DETERMINING AT LEAST ONE PROCESS VARIABLE

(75) Inventors: Sascha D'Angelico, Rümmingen (DE); Simon Tempel, Gundelfingen (DE)

(73) Assignee: ENDRESS + HAUSER GMBH + CO. KG, Maulburg (DE)

( * ) Notice: Subject to any disclaimer, the term of this patent is extended or adjusted under 35 U.S.C. 154(b) by 679 days.

(21) Appl. No.: 13/519,513

(22) PCT Filed: Nov. 11, 2010

(86) PCT No.: PCT/EP2010/067257
§ 371 (c)(1),
(2), (4) Date: Jun. 27, 2012

(87) PCT Pub. No.: WO2011/079999
PCT Pub. Date: Jul. 7, 2011

(65) Prior Publication Data
US 2012/0285239 A1    Nov. 15, 2012

(30) Foreign Application Priority Data

Dec. 29, 2009 (DE) .................. 10 2009 060 837
Mar. 5, 2010 (DE) .................. 10 2010 002 608

(51) Int. Cl.
*G01N 25/00* (2006.01)
*G01N 23/00* (2006.01)
(Continued)

(52) U.S. Cl.
CPC ........ *G01F 23/2967* (2013.01); *G01F 25/0061* (2013.01); *G01K 7/08* (2013.01); *G01K 13/00* (2013.01); *G01N 9/002* (2013.01); *G01N 11/16* (2013.01)

(58) Field of Classification Search
CPC .................................................... G01N 25/00

USPC ..................................... 73/290 R, 290 V, 295
See application file for complete search history.

(56) References Cited

U.S. PATENT DOCUMENTS 3,712,117 A    1/1973   Fitzgerald et al.
4,483,631 A   11/1984   Kydd
(Continued)

FOREIGN PATENT DOCUMENTS

DE    2332015 A    1/1975
DE    3326849 A1   7/1984
(Continued)

OTHER PUBLICATIONS

German Search Report in corresponding German Application No. 10 2010002608.5, dated Oct. 28, 2010.
(Continued)

*Primary Examiner* — Hezron E Williams
*Assistant Examiner* — Hoang Nguyen
(74) *Attorney, Agent, or Firm* — Bacon & Thomas, PLLC

(57) ABSTRACT

An apparatus and method for determining at least one process variable of a medium in a container or in a pipeline. The apparatus including: at least a first element and a second element, which are necessary components of the apparatus for determining the process variable and which contact at a contact location, which is exposed to a process temperature. The first element comprises a first material, and the second element comprises a second material. The first material and the second material are selected and matched to one another in such a manner that at the contact location between the first material and the second material a thermovoltage dependent on the difference between the process temperature and a reference temperature arises; and a temperature determining unit measures the thermovoltage and determines the process temperature therefrom.

10 Claims, 2 Drawing Sheets

(51) Int. Cl.
  *G01F 23/296* (2006.01)
  *G01F 25/00* (2006.01)
  *G01K 7/08* (2006.01)
  *G01K 13/00* (2006.01)
  *G01N 9/00* (2006.01)
  *G01N 11/16* (2006.01)

(56) References Cited

U.S. PATENT DOCUMENTS

| | | | | |
|---|---|---|---|---|
| 5,408,168 | A | * | 4/1995 | Pfandler ............. 318/642 |
| 5,625,343 | A | * | 4/1997 | Rottmar ............. 340/620 |
| 6,054,678 | A | * | 4/2000 | Miyazaki ............. 219/237 |
| 6,845,663 | B2 | * | 1/2005 | Lopatin et al. ............. 73/290 V |
| 6,920,787 | B2 | * | 7/2005 | Brutschin et al. ............. 73/290 V |
| 6,938,475 | B2 | * | 9/2005 | Lopatin ............. 73/290 V |
| 7,043,981 | B2 | * | 5/2006 | Kuhny et al. ............. 73/290 V |
| 7,926,345 | B2 | * | 4/2011 | Kaercher et al. ............. 73/295 |
| 8,752,426 | B2 | * | 6/2014 | Wimberger et al. ............. 73/290 R |
| 2006/0131994 | A1 | * | 6/2006 | D'Angelico et al. ............. 310/317 |

FOREIGN PATENT DOCUMENTS

| | | |
|---|---|---|
| DE | 4017968 A1 | 12/1991 |
| DE | 19526975 A1 | 1/1997 |
| DE | 19810519 A1 | 9/1998 |
| DE | WO2007073837 * | 5/2007 |
| DE | 102005062813 A1 | 7/2007 |
| DE | 102006007199 A1 | 8/2007 |
| EP | 0282251 A2 | 9/1988 |
| EP | 1261437 B1 | 5/2005 |
| GB | 2219661 A | 12/1989 |
| WO | 97/21082 A1 | 6/1997 |
| WO | 2005/043098 A1 | 5/2005 |
| WO | 2007/073837 A2 | 7/2007 |
| WO | 2007/093197 A1 | 8/2007 |

OTHER PUBLICATIONS

International Search Report in corresponding PCT Application No. PCT/EP2010/067257, dated Jul. 15, 2011.
International Preliminary Report on Patentability and Written Opinion of the International Searching Authority in corresponding PCT Application No. PCT/EP2010/067257, dated Jul. 19, 2012.

* cited by examiner

APPARATUS FOR DETERMINING AT LEAST ONE PROCESS VARIABLE

TECHNICAL FIELD

The present invention relates to an apparatus for determining at least one process variable of a medium in a container or in a pipeline; the apparatus comprises at least a first element and a second element, which are necessary components of the apparatus for determining the process variable and which contact at a contact location, which is exposed to a process temperature $T_p$. The apparatus, for example, is a measuring device for determining fill level, density, viscosity, or pressure of a medium.

BACKGROUND DISCUSSION

In measurements technology, a number of different measuring devices are known for determining or monitoring one or more process variables of a medium. For determining the reaching of a predetermined fill level or for monitoring a minimum or maximum fill level of a liquid in a container, among others, vibronic measuring devices are applied, placed at the height in the container to be monitored.

As a rule, vibronic measuring devices have two fork-like tines, which are excited to opposite phase oscillations at the resonance frequency by a drive unit via a membrane. Likewise, so called membrane oscillators without an additional oscillatable unit, or single rods are known. The drive occurs, in such case, via piezoelectric elements. If the oscillatory system is covered by the measured medium, the oscillation is damped and the oscillation frequency decreases, whereby the reaching of the limit level is signaled. Such vibronic measuring devices having an oscillatory fork for fill level detection of liquids are developed by the assignee under the mark LIQUIPHANT and are available and in a great variety of embodiments. The construction of a LIQUIPHANT measuring device is described, for example, in the document EP 1261437 B1.

The density of the measured medium can also be determined with said vibronic measuring devices. The higher the density of a liquid, the lower is the resonance frequency, with which the oscillatory system oscillates. The resonance frequency is, however, temperature dependent, so the temperature of the medium must also be determined for a density determination. Besides this application, a number of additional applications are known, in which, besides the fill level, the determining and monitoring of the process temperature is also required, for example, for detecting the reaching of a maximum allowable process temperature for a sensor.

Until now, a temperature measurement has been possible, for example, by bringing an additional temperature sensor into contact with the container externally, i.e. outside of the fill level or density measuring device, via a separate process connection. For a density measurement compensated for temperature, the temperature sensor and the density measuring device have been connected to the evaluation computer. Each additional process connection poses an additional risk relative to the seal and hygiene of the process, so that it is desirable to integrate the temperature measurement in a measuring device required anyway, and thus save an additional process connection.

Integration of the temperature sensor in a process-near area of the sensor housing of a vibronic fill level measuring device is difficult due to the way in which the piezoelectric driving/receiving unit is mounted. This driving/receiving unit is introduced in the sensor housing on the side of the sensor housing, from which the oscillatable unit faces away. If the temperature sensor is secured on the housing wall of the sensor, it forms, in such case, a hindrance, e.g. for the mounting of the piezoelements. The further the temperature sensor is removed from the process, however, the greater the temperature determined by it deviates from the process temperature.

Document DE 102006007199 A1 describes a vibration-type limit switch, in which a temperature determining unit is introduced between the elements of the transmitting/receiving unit. In the still unpublished German patent application 102009029490.2, temperature sensors are introduced in process-near elements of a fill level measuring device. The disadvantage of these solutions is that they complicate the manufacture of the measuring device.

SUMMARY OF THE INVENTION

An object of the invention is to provide an apparatus for determining at least one process variable of a medium as well as a method, with either of which, or both, apparatus and/or method, it is possible, moreover, to determine the process temperature in a simple manner.

The object relative to apparatus is achieved by features including that the first element comprises a first material and has a first connection line, which contacts the first element with a first end region, that the second element comprises a second material and has a second connection line, which contacts the second element with a first end region, that a second end region of the first connection line and a second end region of the second connection line are led to a temperature determining unit, which is exposed to a reference temperature $T_{ref}$, that the first material and the second material are selected and matched to one another in such a manner that at the contact location between the first material and the second material a thermovoltage $U_{th}$ dependent on the difference between the process temperature $T_p$ and the reference temperature $T_{ref}$ arises, and that the temperature determining unit measures the thermovoltage $U_{th}$ and determines the process temperature $T_p$ therefrom.

The required elements for temperature measurement are thus mainly components of the measuring device already present, supplemented by connection wires or contact lines in order to enable the measuring of the thermovoltage. The materials of two suitable components of the measuring device are selected in such a manner that a thermovoltage between them results. This is proportional to the temperature difference between the process temperature and the reference temperature and dependent on the difference of the Seebeck coefficients of the materials. If the reference temperature and the process temperature are identical, the thermovoltage is zero. Thus, no temperature measuring element is introduced separately into the measuring device, but, a thermocouple is formed from components already present and necessary for the functioning of the measuring device.

In a first embodiment of the invention, the second material is stainless steel and the first material is essentially a nickel chromium compound.

In a preferred embodiment of the invention, the apparatus is a fill level measuring device for determining and/or monitoring a limit fill level of a medium in a container or a pipeline, including: an essentially tubular sensor housing, wherein one of the two ends of the sensor housing is embodied as a membrane; an oscillatable element placed on the outside of the membrane, which oscillatable element forms an oscillatable unit with the membrane; a driving/receiving unit; a nose, which is arranged as a contact piece between the driving/receiving unit and the membrane and contacts the membrane at the contact location; a clamping apparatus, which presses the driving/receiving unit toward the membrane; and a control/evaluation unit; wherein the driving/receiving unit excites the oscillatable unit to execute mechanical oscillations, and wherein the control/evaluation unit evaluates the amplitude, frequency, and/or phase of the oscillations of the oscillatable unit, and the nose and the membrane are embodied in such a manner that they form a thermocouple.

In contrast to solutions of the state of the art, no temperature sensor is introduced in the already narrow space in the area of the drive unit. Rather, the existing elements nose and membrane or sensor housing are given another function. The membrane is part of the sensor housing or secured on the sensor housing, for example, by welding, in the form of a separate component. Since, in each case, it is a fixed connection and the materials of the membrane and sensor housing are identical, the thermocouple is not only formed by the membrane alone, but, also by the sensor housing. Only a connection line to be led from the nose through the clamping apparatus into the area of the sensor housing lying behind the clamping apparatus is a supplemental element on the process facing side of the sensor housing. The materials of the nose and sensor housing or membrane are correspondingly chosen for this additional function. The additional elements needed for determining the temperature of the medium such as the temperature sensor for determining the reference temperature $T_{ref}$, as well as the temperature determining unit, are introducible in the part of the sensor housing, which offers enough space, lying behind the clamping apparatus.

In an additional further development of the invention, the nose and the first connection line are manufactured from a first material, which has a first Seebeck coefficients a1, and the membrane and the second connection line are manufactured from a second material, which has a second Seebeck coefficients a2, wherein a1 is different from a2. The Seebeck coefficient is a material constant having the units, voltage over temperature. The thermovoltage, which can form between two materials, depends on the difference of these values, i.e. the larger the difference |a1−a2|, the larger the measurement effect.

A further development of the invention provides that the temperature determining unit is arranged on the side of the clamping apparatus facing away from the driving/receiving unit. As a rule, the electronics of the measuring device are located here. Within the sensor housing, especially on the side facing away from the process, the temperatures arising generally lie within a limited range compared to the range, in which the process temperatures lie. The temperature determining unit is, thus, protected from very high process temperatures, which could negatively influence its functional ability.

In an embodiment, the temperature determining unit is integrated in the control/evaluation unit. For example, it is, in such case, a microcontroller having an integrated temperature sensor.

In an additional embodiment, the driving/receiving unit comprises piezoelectric elements and the first connection line is led through the clamping apparatus together with the contact lines of the piezoelectric elements. There are known embodiments, in which the contact lines of the piezoelectric elements are applied on a flexible circuit board. The connection line is, in this case, preferably embodied as an additional conductive trace on the same circuit board.

Furthermore, the invention relates to a method for determining the process temperature using a measuring device for determining a process variable different from temperature in a container or a pipeline, which measuring device includes at least one first element and a second element, which are necessary components of the measuring device for determining the process variable and which are in contact at a contact location exposed to the process temperature $T_p$.

The object, as regards the method, is achieved by features including that the first element is manufactured from a first material M1 and the second element is manufactured from a second material M2, the first element is contacted with a first connection line and the second element is contacted with a second connection line, the connection lines are led to a temperature determining unit, which is exposed to a reference temperature $T_{ref}$, the first material and the second material are selected and matched to one another in such a manner that a thermovoltage $U_{th}$ forms between the first element of the first material and the second element of the second material, which thermovoltage $U_{th}$ is dependent on the difference between the process temperature $T_p$ and the reference temperature $T_{ref}$, the thermovoltage $U_{th}$ is measured in the temperature determining unit, and the process temperature $T_p$ is determined from the thermovoltage $U_{th}$.

In an embodiment of the method of the invention, the first material and the second material are selected in such a manner that their Seebeck coefficients differ from one another.

In an especially advantageous embodiment of the method for determining the temperature, a vibronic fill level measuring device is used, comprising: an essentially tubular sensor housing, wherein one of the two ends of the sensor housing is embodied as a membrane; an oscillatable element placed on the outside of the membrane, which oscillatable element forms an oscillatable unit with the membrane; a driving/receiving unit; a nose, which is arranged as a contact piece between the driving/receiving unit and the membrane and contacts the membrane at the contact location; a clamping apparatus, which presses the driving/receiving unit toward the membrane; and a control/evaluation unit; wherein the driving/receiving unit excites the oscillatable unit to execute mechanical oscillations, and wherein the control/evaluation unit evaluates amplitude, frequency, and/or phase of the oscillations of the oscillatable unit; and a thermocouple is formed from the nose and the membrane.

BRIEF DESCRIPTION OF THE DRAWING

The invention will now be explained in greater detail based on the appended drawing, the figures of which show as follows.

Figure 1:
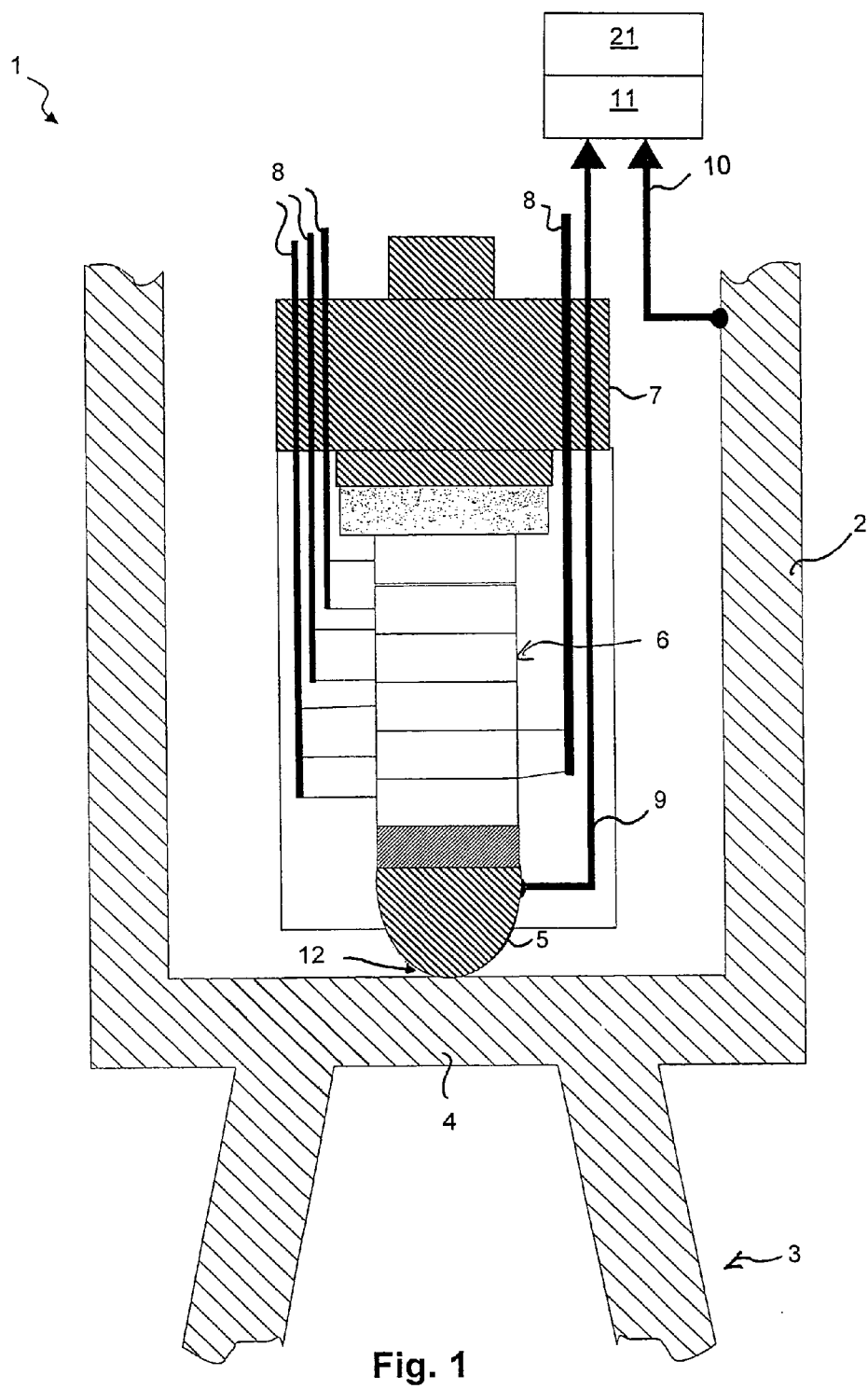
FIG. 1 is a representation of a sectional illustration of a detail of a fill level measuring device.

As an example of an embodiment of the invention, a section through the process-side end region of the fill level measuring device 1 having an oscillatable unit is presented schematically in FIG. 1. The oscillatable unit is formed by the membrane 4 and an oscillatable element 3 formed as a oscillatory fork solidly connected to membrane 4. Membrane 4 is a part of the sensor housing 2 and closes the process-side end region. Oscillatable element 3, sensor housing 2 and membrane 4 are manufactured from the same material, preferably stainless steel. The driving/receiving unit 6 is arranged in the interior of sensor housing 2. In this example of an embodiment, driving/receiving unit 6 is a stack drive composed of piezoelectric elements and is clamped between a pressure screw 7 and a nose 5. Instead of pressure screw 7, other securement means are also conceivable, for example, a yoke. Via nose 5, the force of driving/receiving unit 6 is transmitted to membrane 4, which, in turn, excites oscillatable element 3 to mechanical oscillations. Nose 5 is preferably hemispherical and contacts membrane 4 on a small area at the contact location 12.

Nose 5 and membrane 4, respectively sensor housing 2, are manufactured of different materials and form a thermocouple. In this embodiment, thus, nose 5 is the first element comprising the first material M1 and membrane 4 is the second element comprising the second material M2. A thermovoltage $U_{th}$ forms at contact location 12. For measuring the thermovoltage, nose 5 is connected to a first connection line 9, which comprises the same material as nose 5. In the same way, membrane 4 is connected via sensor housing 2 to a second connection line 10, which likewise comprises the same material as sensor housing 2. Both connection lines 9, 10 are led to a temperature determining unit 11. Temperature determining unit is located preferably in an area of the sensor housing remote from the process so that the there reigning reference temperature $T_{ref}$ differs from the temperature $T_p$, which corresponds to temperature of the process or of the medium to be determined, reigning at contact location 12. Especially when the oscillatable unit 3 is covered by the process medium, the process temperature $T_p$ corresponds to the temperature of the medium. For the case, in which the temperatures $T_{ref}$ and $T_p$ do not differ, a thermovoltage $U_{th}$ does not arise and the measured value of the thermovoltage is zero. Temperature determining unit 11 is a microcontroller, for example. Such electronic components are sensitive to high temperatures so that it is advantageous when temperature determining unit 11 is thermally insulated from the process. Preferably, temperature determining unit 11 is integrated into the sensor electronics, so that no additional component for temperature determining unit 11 is necessary.

The greater the thermovoltage, the greater is the difference between the Seebeck coefficient a1 of the material of nose 5 and the Seebeck coefficient a2 of the material of sensor housing 2. In order to be able to determine the process temperature $T_p$ in the case of small temperature differences $dT=|T_p-T_{ref}|$ between the process and the site of temperature determining unit 11, it is consequently advantageous, when the magnitude of the difference a1–a2 is as large as possible. If membrane 4 and sensor housing 2 are manufactured of stainless steel, e.g. stainless steel 3161, it is advantageous to manufacture nose 5 of a nickel chromium compound.

Temperature determining unit 11 is a separate electronics module or integrated into the control/evaluation unit 21. Advantageously, temperature determining unit 11 is a microcontroller, which has an integrated temperature sensor, so that the reference temperature $T_{ref}$ at the site of temperature determining unit 11 is known at any time without a separate temperature sensor.

Figure 2:
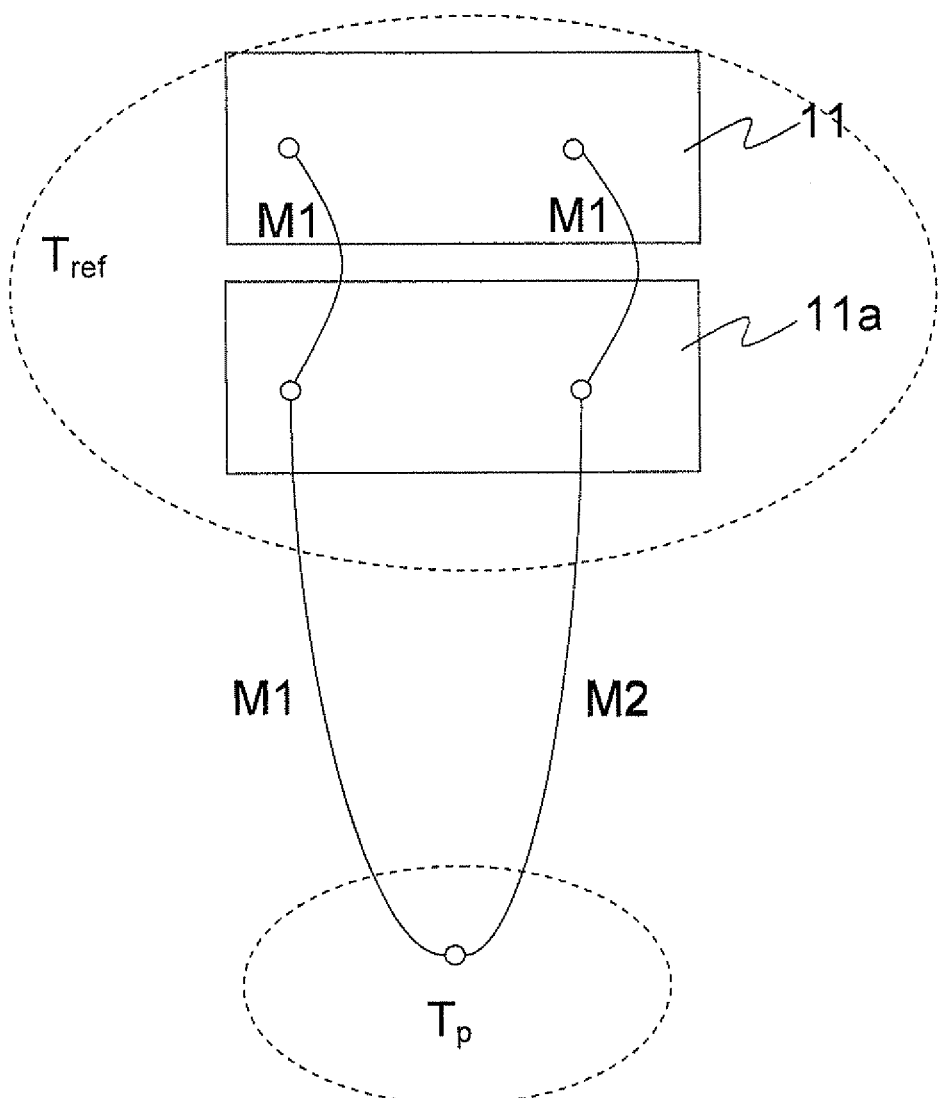
FIG. 2 is a schematic representation of the measuring principle.

FIG. 2 shows a sketch of the measuring principle for determining the process temperature $T_p$. At the contact location, first material M1 and second material M2 meet with a process temperature $T_p$ to be determined. Connection lines comprising the same material lead, in each case, away from the process and toward a comparison measuring point 11a at a reference temperature $T_{ref}$. The end points in the comparison measuring point 11a are led via connection wires, which comprise material M1 in this example, to temperature determining unit 11 in the form of a microcontroller, and the potential difference between the end points of the connection wires is determined.

Comparison measuring point 11a can also lie, in such case, within microcontroller 11. The potential difference is equal to thermovoltage $U_{th}$. Process temperature $T_p$ results from the value of thermovoltage $U_{th}$:

$$T_p=U_{th}/(a2-a1)+T_{ref}$$

Expressed in words, the process temperature results from the sum of the reference temperature at the site of the temperature determining unit and the quotient of the thermovoltage and the difference of the Seebeck coefficients of the two materials.

LIST OF REFERENCE CHARACTERS

1 fill level measuring device
2 sensor housing
3 oscillatable element
4 membrane/second element
5 nose/first element
6 driving/receiving unit
7 pressure screw
8 contact lines
9 first connection line
10 second connection line
11 temperature determining unit
11a comparison measuring point
12 contact location
21 control/evaluation unit
M1 first material
M2 second material

The invention claimed is:
1. An apparatus for determining at least one process variable different from temperature of a medium in a container or in a pipeline, at least comprising:
a first element;
a second element, and
a temperature determining unit, wherein:
said first element and said second element are necessary components of the apparatus for determining the process variable and which contact, at a contact location, which is exposed to a process temperature,
said first element comprises a first material and has a first connection line, which contacts said first element with a first end region;
said second element comprises a second material and has a second connection line, which contacts said second element with a first end region;
a second end region of said first connection line and a second end region of said second connection line are led to said temperature determining unit, which is exposed to a reference temperature;
said first material and said second material are selected and matched to one another in such a manner that at the contact location between said first material and said second material a thermovoltage dependent on the difference between the process temperature and said reference temperature arises; and
said temperature determining unit measures the thermovoltage and determines the process temperature therefrom.
2. The apparatus as claimed in claim 1, wherein:
said second material is stainless steel and said first material is essentially a nickel chromium compound.
3. The apparatus as claimed in claim 2, wherein:
the apparatus is a fill level measuring device for determining and/or monitoring a limit fill level of a medium in a container or a pipeline, further comprising:
an essentially tubular sensor housing, wherein one of the two ends of said essentially tubular sensor housing is embodied as a membrane;
an oscillatable element placed on the outside of said membrane, which oscillatable element forms an oscillatable unit with said membrane;
a driving/receiving unit;
a nose, which is arranged as a contact piece between said driving/receiving unit and said membrane, and which contacts said membrane at said contact location;

a clamping apparatus, which presses said driving/receiving unit toward said membrane; and a control/evaluation unit, wherein:

said driving/receiving unit excites said oscillatable unit to mechanical oscillations;

said control/evaluation unit evaluates the amplitude, frequency, and/or phase of the oscillations of said oscillatable unit; and said nose and said membrane are embodied in such a manner that they form a thermocouple.

4. The apparatus as claimed in claim 3, wherein:

said nose and said first connection line are manufactured from a first material, which has a first Seebeck coefficient a1; and said membrane and said second connection line are manufactured from a second material, which has a second Seebeck coefficient a2; and a1 is different from a2.

5. The apparatus as claimed in claim 3, wherein:

said temperature determining unit is arranged on the side of said clamping apparatus facing away from said driving/receiving unit.

6. The apparatus as claimed in claim 3, wherein:

said temperature determining unit is integrated into said control/evaluation unit.

7. The apparatus as claimed in claim 3, wherein:

said driving/receiving unit comprises piezoelectric elements, and, together with the contact lines of said piezoelectric elements, said first connection line is led through said clamping apparatus.

8. A method for determining a process temperature with a measuring device for determining a process variable different from temperature in a container or a pipeline, which measuring device at least comprises a first element, a second element, and a temperature determining unit, where said first element and said second element are necessary components of the measuring device for determining the process variable and which contact at a contact location, which is exposed to the process temperature, the method comprising the steps of:

manufacturing the first element from a first material and the second element from a second material;

contacting the first element with a first connection line and the second element with a second connection line;

leading the connection lines to a temperature determining unit, which is exposed to a reference temperature;

selecting the first material and the second material and matching them to one another in such a manner that a thermovoltage forms between the first element of the first material and the second element of the second material, which thermovoltage is dependent on the difference between the process temperature and the reference temperature;

measuring the thermovoltage in the temperature determining unit; and determining the process temperature from the thermovoltage.

9. The method as claimed in claim 8, wherein:

the first material and the second material are selected in such a manner that their Seebeck coefficients differ from one another.

10. The method as claimed in claim 8, wherein:

a vibronic fill level measuring device is used for determining the process temperature;

the vibronic fill level measuring device comprises: an essentially tubular sensor housing, wherein one of two ends of the sensor housing is embodied as a membrane; an oscillatable element placed on the outside of the membrane, which oscillatable element forms with the membrane an oscillatable unit; a driving/receiving unit; a nose, which is arranged between the driving/receiving unit and the membrane as a contact piece, and contacts the membrane at the contact location; a clamping apparatus, which presses the driving/receiving unit toward the membrane;

a control/evaluation unit;

the driving/receiving unit excites the oscillatable unit to execute mechanical oscillations; and the control/evaluation unit evaluates amplitude, frequency, and/or phase of the oscillations of the oscillatable unit; and a thermocouple is formed by the nose and the membrane.

* * * * *